United States Patent
Tormod

(10) Patent No.: US 8,068,227 B2
(45) Date of Patent: Nov. 29, 2011

(54) METHODS AND APPARATUS FOR MEASURING THE CONCENTRATION OF A SUBSTANCE IN A SOLUTION

(75) Inventor: Stig Tormod, Uppsala (SE)

(73) Assignee: GE Healthcare Bio-Science AB, Uppsala (SE)

( * ) Notice: Subject to any disclaimer, the term of this patent is extended or adjusted under 35 U.S.C. 154(b) by 157 days.

(21) Appl. No.: 12/095,326

(22) PCT Filed: Nov. 28, 2006

(86) PCT No.: PCT/EP2006/011394
§ 371 (c)(1),
(2), (4) Date: May 29, 2008

(87) PCT Pub. No.: WO2007/062800
PCT Pub. Date: Jun. 7, 2007

(65) Prior Publication Data
US 2008/0304048 A1 Dec. 11, 2008

(30) Foreign Application Priority Data
Nov. 29, 2005 (GB) .................................. 0524225.0

(51) Int. Cl.
*G01N 21/33* (2006.01)
*G01N 21/59* (2006.01)

(52) U.S. Cl. ............................ 356/442; 356/432; 356/51

(58) Field of Classification Search .......... 356/432–444, 356/71–73, 328, 334, 51; 250/343, 458.1, 250/459.1, 461.1, 339.09, 339.02
See application file for complete search history.

(56) References Cited

U.S. PATENT DOCUMENTS

| | | | |
|---|---|---|---|
| 4,076,420 A * | 2/1978 | De Maeyer et al. | 356/73 |
| 4,802,768 A * | 2/1989 | Gifford et al. | 356/417 |
| 4,823,354 A * | 4/1989 | Znotins et al. | 372/57 |
| 5,473,162 A * | 12/1995 | Busch et al. | 250/341.6 |
| 5,699,156 A * | 12/1997 | Carver | 356/319 |
| 6,226,084 B1 * | 5/2001 | Tormod | 356/328 |
| 6,426,045 B1 | 7/2002 | Jeng et al. | |
| 6,574,490 B2 * | 6/2003 | Abbink et al. | 600/316 |
| 6,774,368 B2 * | 8/2004 | Busch et al. | 250/339.09 |
| 6,775,001 B2 * | 8/2004 | Friberg et al. | 356/437 |
| 7,550,563 B2 * | 6/2009 | Schwartsburd et al. | 530/350 |
| 2003/0025909 A1 | 2/2003 | Hallstadius | |
| 2005/0074896 A1 | 4/2005 | Tsuda et al. | |
| 2005/0093485 A1 | 5/2005 | Spivak | |
| 2005/0133724 A1 | 6/2005 | Hsieh et al. | |
| 2005/0247888 A1 | 11/2005 | Waluszko | |

FOREIGN PATENT DOCUMENTS

| | | |
|---|---|---|
| JP | 08114432 A * | 5/1996 |
| JP | 2002005826 | 1/2002 |
| WO | WO 2005/031881 | 4/2005 |

* cited by examiner

*Primary Examiner* — Sang Nguyen

(57) ABSTRACT

The present invention relates to methods and apparatus for detecting and measuring the concentration of a substance in a solution, the substance having an absorption at 300 nm or less. The methods and apparatus have particular utility in detecting and measuring the concentration of proteins and nucleic acids.

9 Claims, 6 Drawing Sheets

SEQUENCE LISTING

<160> NUMBER OF SEQ ID NOS: 1

<210> SEQ ID NO 1
<211> LENGTH: 20
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 1
ataccgatta agcgaagttt                                                    20

METHODS AND APPARATUS FOR MEASURING THE CONCENTRATION OF A SUBSTANCE IN A SOLUTION

CROSS-REFERENCE TO RELATED APPLICATIONS

This application is a filing under 35 U.S.C. §371 and claims priority to international patent application number PCT/EP2006/011394 filed Nov. 28, 2006, published on Jun. 7, 2007, as WO 2007/062800, which claims priority to patent application number 0524225.0 filed in Great Britain on Nov. 29, 2005.

FIELD OF THE INVENTION

The invention relates to methods and apparatus for detecting and for measuring the concentration of a substance in a solution with an absorption at 300 nm or less.

BACKGROUND OF THE INVENTION

Many substances absorb ultra violet or visible light due to their chemical composition. The absorption of light by substances has been used as the basis for detecting the presence of, and measuring the concentration of, such substances for many years. The concentration of the substance can be determined by use of the Beer Lambert Law:

$$A = Ebc$$

where A is absorbance,
E is the molar absorbtivity with units of $L\ mol^{-1}\ cm^{-1}$,
b is the path length of the sample defined in cm; and
c is the concentration of the compound in solution, expressed in $mol\ L^{-1}$.

The Emax represents the maximum absorption of a substance at a given wavelength.

The UV region can be considered to consist of light of wavelength in the region of 1 nm to 400 nm, light of wavelength of 180 mm to 300 nm being known as 'deep UV'.

Most analytical instruments for detecting substances which absorb in the deep ultra violet (UV) region use a mercury-lamp, deuterium lamp or xenon flash lamp as a light source. One example of such an instrument is a flow cell in which a solution containing one or more UV absorbing substances is passed between a UV light source (e.g. a mercury-lamp) and a UV detector (e.g. a photomultiplier or a photodiode) and changes in the intensity of UV light reaching the detector are related to the concentration of UV absorbing substances in the solution.

The detection of proteins, nucleic acids and peptides are of great importance in many sectors, including the environmental, biological and chemical sciences. Proteins have mainly two absorption peaks in the deep UV region, one very strong absorption band with a maximum at about 190 nm, where peptide bonds absorb, and another less intense peak at about 280 nm due to light absorption by aromatic amino acids (e.g. tyrosine, tryptophan and phenylalanine).

Nucleic acids absorb UV light at around 260 nm, some of the subunits of nucleic acids (purines) having an absorbance maximum slightly below 260 nm while others (pyrimidines) have a maximum slightly above 260 nm.

Almost all proteins have a maximum absorbance at about 280 nm due to the content of the light absorbing aromatic amino acids. The light source in the detectors of analytical systems used to detect and measure protein concentrations has historically been the mercury-line lamp. Mercury produces light with a wavelength of 254 nm but not at 280 nm, so a fluorescence converter is needed to transform the 254 nm light produced by the mercury lamp to longer wavelengths and a band pass filter is used to cut out a region around 280 nm. Mercury lamps have relatively short lifetimes and can prove unstable with time; furthermore, the disposal of these lamps can lead to environmental problems. The other lamps used to generate ultra violet light, such as the deuterium and the xenon flash lamps, disadvantageously require high voltages, need complicated electronics and often prove unstable with time. All of the currently used ultra violet light sources are relatively large and are consequently unsuitable for miniaturisation of analytical instruments. Moreover, all of the lamps generate significant amounts of heat due to the high voltages required for their operation.

Recently light emitting diodes (LED) of type AlGaN/GaN with emissions in the 250 nm to 365 nm range have been developed. Sensor Electronic Technology, Inc. (Columbia, S.C., USA) have pioneered the development and use of these UV light emitting diodes, particularly for irradiating and sterilising fluids such as biologically contaminated water (e.g. US 2005/0093485). Other groups have also employed UV light emitting diodes for water purification systems (e.g. Phillips Electronics, WO2005/031881).

Light emitting diodes (LEDs), which emit in the visible region of the spectrum, have been used for indirect photometric detection (Johns C., et al. (2004) Electrophoresis, 25, 3145-3152) and fluorescence detection of substances in capilliary electrophoresis (Tsai C., et al. (2003) Electrophoresis, 24, 3083-3088). King et al. (Analyst (2002) 127, 1564-1567) have also reported the use of UV light-emitting diodes which emit at 379.5 nm for indirect photometric detection of inorganic anions.

The use of deep UV light emitting diodes as light sources in detection systems for nucleic acids is disclosed in US2005/0133724. However, although detection systems employing LEDs are disclosed, there are no experimental data to indicate that the proposed systems were indeed successfully employed to measure nucleic acid levels in polymerase chain reaction assay. The system described would lack sensitivity, linearity, and dynamic range because there is no use of a band pass filter or a beam splitter and reference detector; LEDs are very sensitive to minute changes in temperature, changes of the order of one hundredth of a degree Centigrade causing a drift in the baseline. Furthermore, the system lacks a band pass filter which acts to both narrow the bandwidth and block light in the visible region of the spectrum. A narrow bandwidth compared to the natural bandwidth of the sample, preferable a ratio of 1 to 10, provides a good linearity of the response and a broad dynamic range. (Practical Absorbance Spectrometry. Ed. A Knowles and C. Burgess, Chapman and Hall, New York)

JP2002005826 discloses a system for measuring ozone concentration. However, no experimental data that show the linearity and dynamic range are provided. The system uses a solid state emitter, which is composed of a diamond semiconductor thin film, to emit ultraviolet light with an emission peak of wavelength 240 to 270 nm. The emission spectrum at half value width of the UV peak is somewhat narrower than the half value width of the peak of the absorption spectrum of ozone (emission maximum approximately 254 nm). However, while this may be sufficient to measure ozone concentrations, the lack of a band pass filter which can reduce the band width to, for example, one tenth of the half value width of the ozone absorbtion peak will significantly reduce the linearity and dynamic range of the detector (Practical Absorbance Spectrometry. Ed. A Knowles and C. Burgess, Chapman and Hall, New York). This system also lacks a reference photo detector, so no measurement of the intensity of the emitted light is made. This means that compensation of variations of the emitted intensity due to changes in temperature is not possible.

The present invention addresses the aforementioned problems with the currently available light sources used in analytical systems for detecting and/or for measuring the concentration of a substance in a solution with an absorption of 300 nm or less.

SUMMARY OF THE INVENTION

It will be understood that the term 'substance', as used herein, refers to any chemical entity. In particular, it includes organic compounds and inorganic compounds. Examples of organic compounds include, but are not limited to, proteins, peptides, carbohydrates, lipids, nucleic acids, protein nucleic acids, drug candidates and xenobiotics. Examples of inorganic compounds include metal salts (e.g. ferric sulphate, copper chloride, nickel nitrate).

In a first aspect of the present invention, there is provided a method for measuring the concentration of a substance in a solution, the substance having an absorption at 300 nm or less, the method comprising the steps of
  i) transmitting ultraviolet light of wavelength 300 nm or less from a light source through a band pass filter;
  ii) passing said ultraviolet light emanating from said band pass filter through a beam-splitter;
  iii) diverting a first portion of the light by the beam-splitter and quantifying the electromagnetic radiation of said first portion with a reference detector to obtain a reference value;
  iv) irradiating a known path length of said solution with a second portion of the light passing through the beam splitter;
  v) quantifying the electromagnetic radiation transmitted through the solution with a sample detector to obtain a sample value; and
  vi) calculating the absorbance (A) from said sample value and said reference value.
characterised in that said light source is a light emitting diode which emits light of wavelength of 300 nm or less.

According to a second aspect of the present invention, there is provided an apparatus for measuring the concentration of a substance in a solution, the substance having an absorption at 300 nm or less, comprising
  i) a cell of known path length for containing said solution, said cell being transparent to light of wavelength of 300 nm or less;
  ii) a light source;
  iii) a band pass filter;
  iv) a beam splitter for dividing light into a first portion and a second portion;
  v) a reference detector for detecting said first portion of electromagnetic radiation diverted by said beam splitter;
  vi) a sample detector for detecting said second portion of the electro magnetic radiation transmitted through the solution;
characterised in that said light source is a light emitting diode which emits light of wavelength of 300 nm or less.

According to a third aspect of the present invention, there is provided the use of the apparatus as hereinbefore described for the first and second aspects of the invention for measuring the concentration of a substance selected from the group consisting of protein, peptide and nucleic acid.

DETAILED DESCRIPTION OF THE INVENTION

Figure 1:
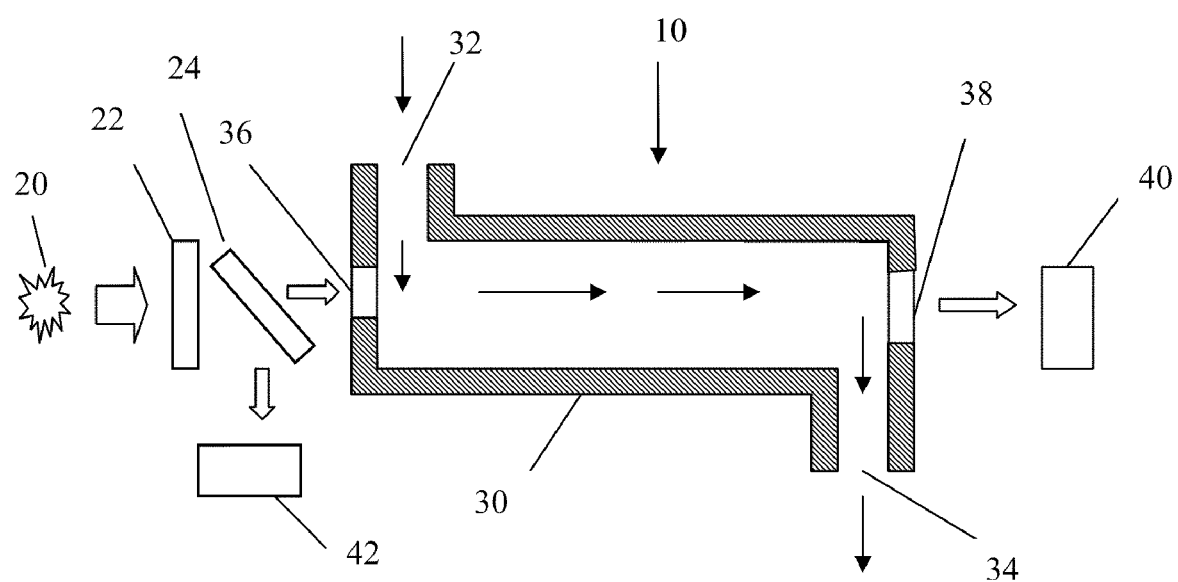
FIG. 1 is a schematic diagram showing a first embodiment of an apparatus according to the invention for measuring the concentration of a substance in a solution having an absorption at 300 nm or below.

FIG. 1 is a schematic representation of one embodiment of an apparatus according to the invention taken in transverse section. The apparatus (10) comprises a UV light emitting diode (20), a flow cell (30) with an inlet (32) and an outlet (34) and photo-detectors (40,42) which can either be UV sensitive photo multipliers or UV sensitive photo diodes. The apparatus consists of a band pass interference filter (22) which is an optical filter that reflects one or more spectral bands or lines and transmits others, while maintaining a low coefficient of absorption for the UV wavelengths of interest. The bandwidth of the filter is preferably less than 10 nm, the smaller the better, to give a good linearity and large dynamic range. The light then passes through a beam-splitter (24) which diverts some of the light onto a reference photo detector (42) while the remainder is directed through the window (36) into the solution within the flow cell (10). The beam-splitter (24) and reference photo detector (42) are used to follow any intensity changes in the light emitting diode (20) and thus avoid the need for carefully thermostating the light emitting diode. The flow cell (30) has windows (36 and 38) which are made from a UV transparent material such as sapphire, quartz or synthetic fused silica and is of a known path length.

A solution containing a substance with an absorption at 300 nm or less (e.g. a protein or nucleic acid) is passed through the flow cell (30), as indicated by the single arrows, via the inlet (32) and the outlet (34). A UV light emitting diode (20) is used to irradiate the solution in the flow cell (30), the light entering the flow cell (30) through the UV transparent window (36), as indicated by the block arrows. Light passing through the solution (indicated by the block arrow) and window (38) is then detected by the photo-detector (40).

The wavelength of UV light employed to irradiate the sample can be selected by either the use of an appropriate LED which emits at a specific wavelength of UV light (for example, a UVTOP® 260 nm or 280 nm LED) or by means of a light emitting diode with a broader emission spectrum in the deep UV. To narrow the bandwidth of the emitted light and block wavelengths in the visible region a band pass filter is inserted in front of the LED. UVTOP® LEDs are available from Sensor Electronic Technology Inc., SC, USA (e.g. the 'TO-39' package contains a number of UV-light emitting diodes which emit in the range of 250-365 nm).

The concentration of the substance in the solution can then be determined by use of the Beer Lambert Law where the molar absorbtivity (E) of the substance is already known. Alternatively, the concentration of the substance can be determined by use of a dose-response curve which has previously been produced for the substance of interest at a given wavelength (e.g. 280 nm).

Figure 2:
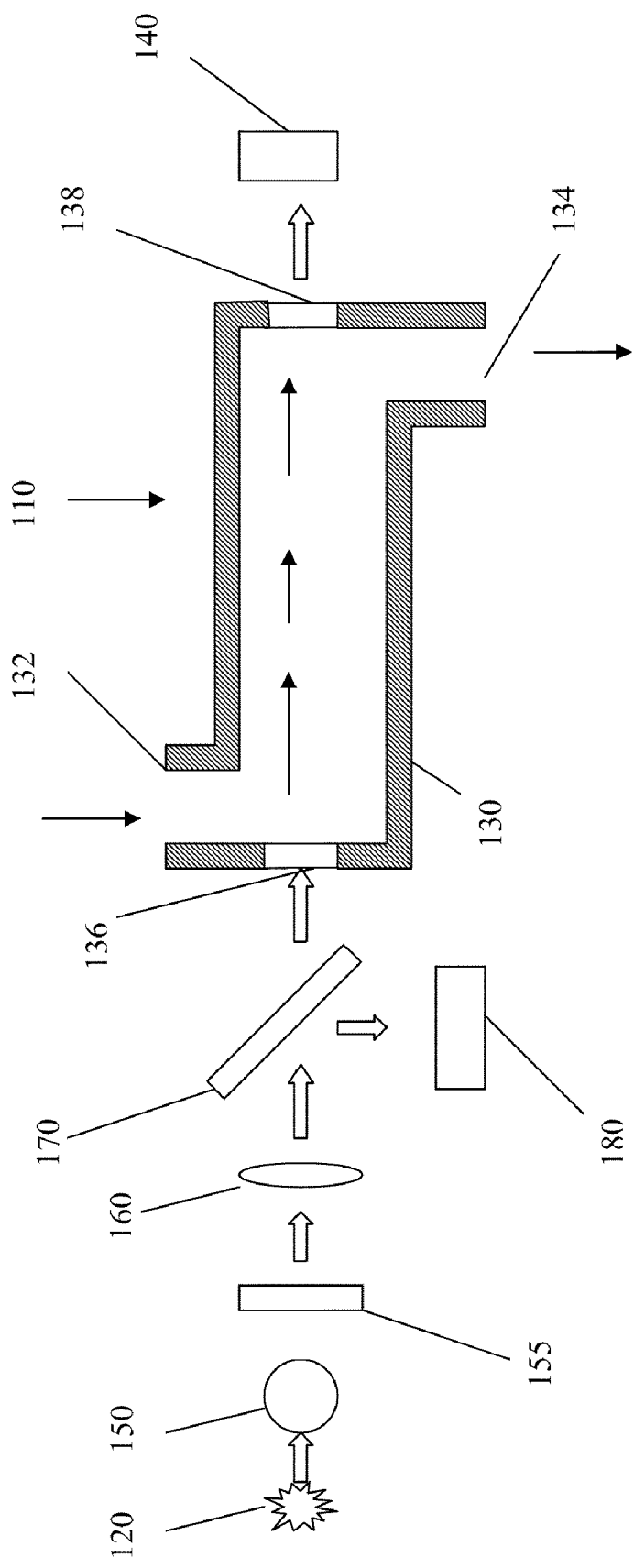
FIG. 2 depicts a second embodiment of an apparatus according to the invention.

Another embodiment of an apparatus (110) according to the invention is shown in transverse section in schematic form in FIG. 2. A solution containing a substance with an absorption at a wavelength of 300 nm or less enters the flow cell (130) through an inlet (132) and passes through the cell, exiting through an outlet (134), as indicated by the single arrows. The flow cell (130) is of known path length and has windows (136 and 138) made of a UV transparent material such as sapphire, quartz or synthetic fused silica.

UV light (block arrows) emanating from a UV light emitting diode (120) is directed through a collimating ball or hemispherical lens (150), a band pass filter (155) and a focusing lens (160) to narrow the band width of the emitted light and to increase light throughput thereby decreasing noise levels. The UV light emitting diode (120) could, for example, be a UVTOP® 260 nm or UVTOP® 280 diode obtained from Sensor Electronic Technology, Inc, SC, USA. The light then passes through a beam-splitter (170) which diverts some of the light onto a reference photo detector (180) while the remainder is directed through the window (136) into the solution within the flow cell (130). The beam-splitter (170) and reference photo detector (180) are used to follow any intensity changes in the light emitting diode (120) and thus avoid the need for carefully thermostating the light emitting diode.

The ultra violet light passing through the solution in the flow cell (130) and exiting from the window (138) is detected by the sample photo-detector (140), as indicated by the block arrows; both of the UV detectors (140 and 180) may be a UV sensitive photomultiplier or a UV sensitive photo diode. The concentration of the substance in the solution can then be determined by use of the Beer Lambert Law where the molar absorbtivity (E) of the substance is already known. Alternatively, the concentration of the substance can be determined by use of a dose-response curve which has previously been produced for the substance of interest at a given wavelength (e.g. 280 nm).

It will be understood by the person skilled in the art that an identical apparatus, having a flow cell (130) of unknown path length, could be used simply to detect the presence of a substance with an absorption at 300 nm or less. The determination or measurement of the concentration of the substance in solution requires knowledge of the path length (cf. Beer Lambert Law).

Figure 3:
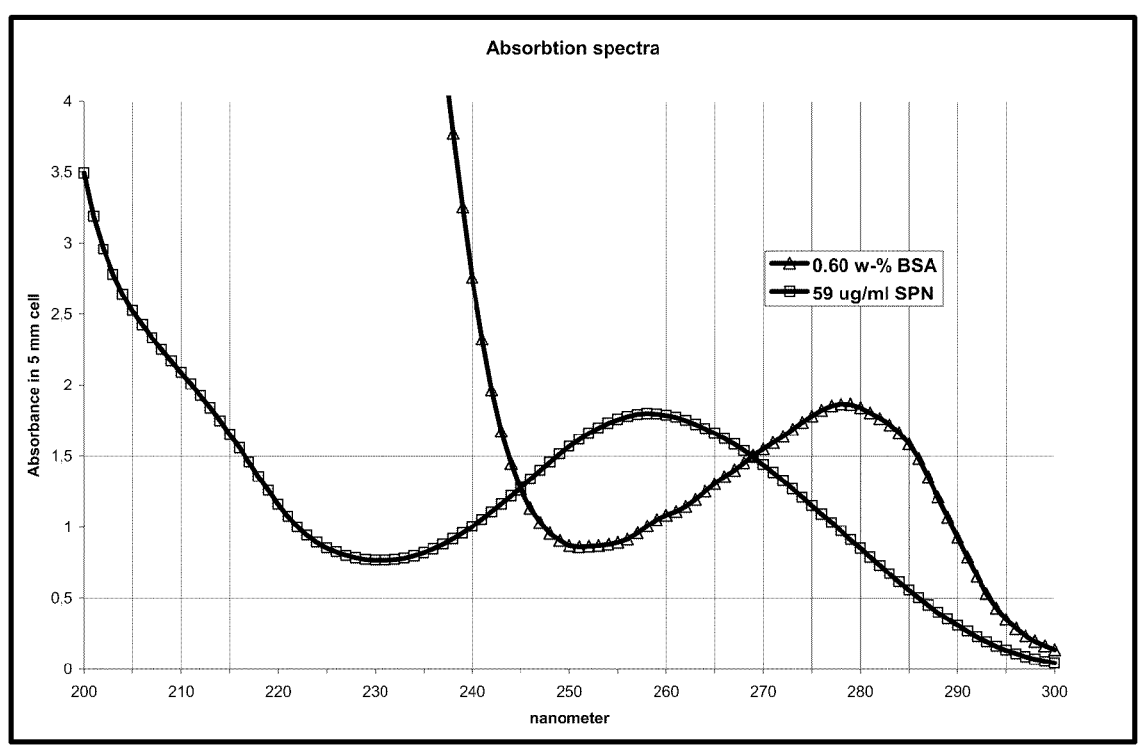
FIG. 3 shows the UV spectra of Bovine Serum Albumin (BSA) and Synthetic Poly Nucleotide (SPN) from 200-300 nm measured using a Perkin Elmer LAMBDA 900 spectrophotometer.

FIG. 3 shows the UV spectra of Bovine Serum Albumin (BSA) and Synthetic Poly Nucleotide (SPN) taken at 200 nm to 300 nm using a Perkin Elmer LAMBDA 900 spectrophotometer (PerkinElmer Life and Analytical Sciences Inc., Boston, Mass., USA). BSA was obtained from Sigma (Sigma-Aldrich Inc, MO, USA). The Synthetic Polynucleotide (SPN) was a 20 mer (5'-ATA CCG ATT AAG CGA AGT TT-3') (SEQ ID NO:1) produced as described by J Shanagar, J. Biochem. Biophys. Methods (2005), 64, 216-225.

The spectra of both BSA (0.6% by weight) and SPN (59 µg/ml) were taken in 20 mM sodium phosphate buffer at pH 7.0. As can be seen from FIG. 3, BSA has an absorbance peak (Emax) at approximately 278 nm while SPN has an absorbance peak (Emax) at approximately 258 nm.

Figure 4:
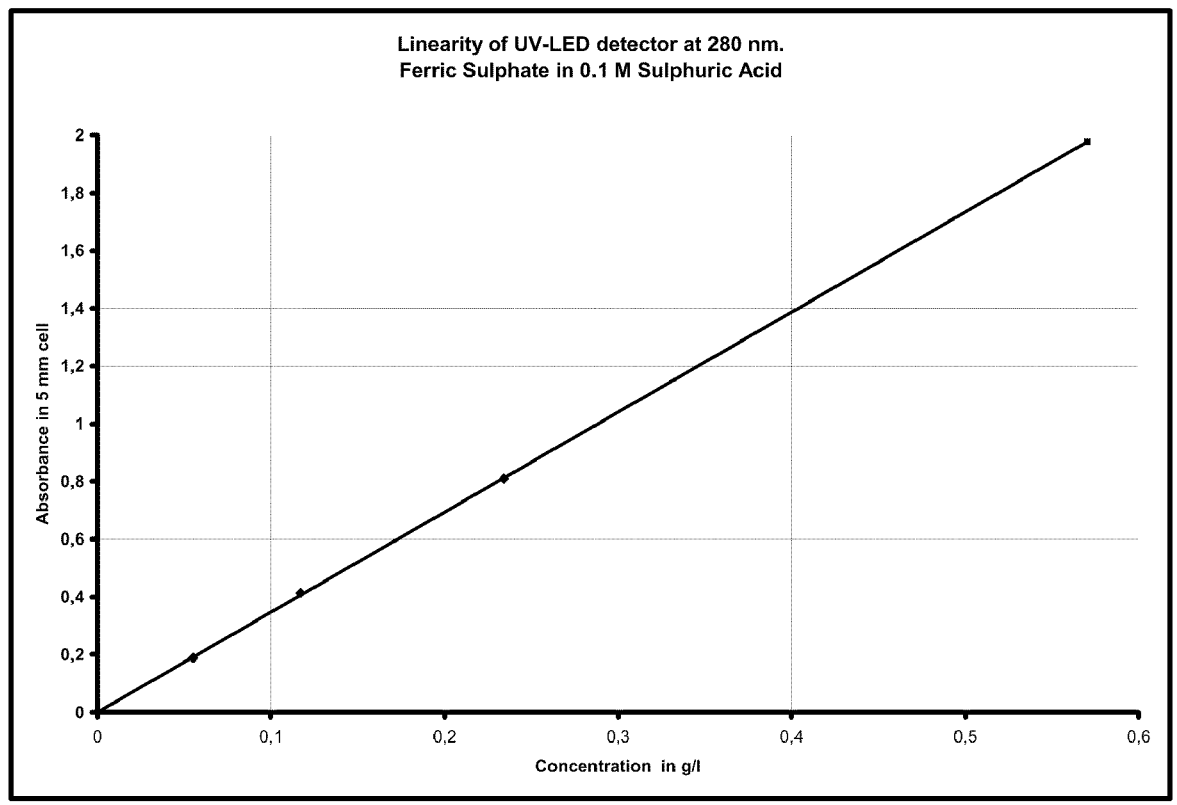
FIG. 4 is a graph demonstrating the linearity of response of a UV-LED detector at 280 nm to a range of ferric sulphate concentrations in 0.1 M sulphuric acid.

FIG. 4 is a graph showing the linearity of the response of the UV-LED detector at 280 nm to a range of concentrations of ferric sulphate in 0.1 M sulphuric acid. Ferric sulphate was diluted in 0.1 M sulphuric acid to prepare a range of concentrations. Ferric sulphate is known to have an absorption in the deep UV. Each solution was irradiated with ultra violet light from a UV-light emitting diode using an apparatus as described in FIG. 2 above and equipped with a UVTOP® 280 UV light emitting diode (Sensor Electronic Technology, Inc., SC, USA) and a band pass interference filter with 7 nm bandwidth centered at 280 nm obtained from Omega Optical Inc., USA. A linear response was seen to increasing concentrations of ferric sulphate over the range of approximately 0.1 to 0.5 g/l (FIG. 4).

Figure 5:
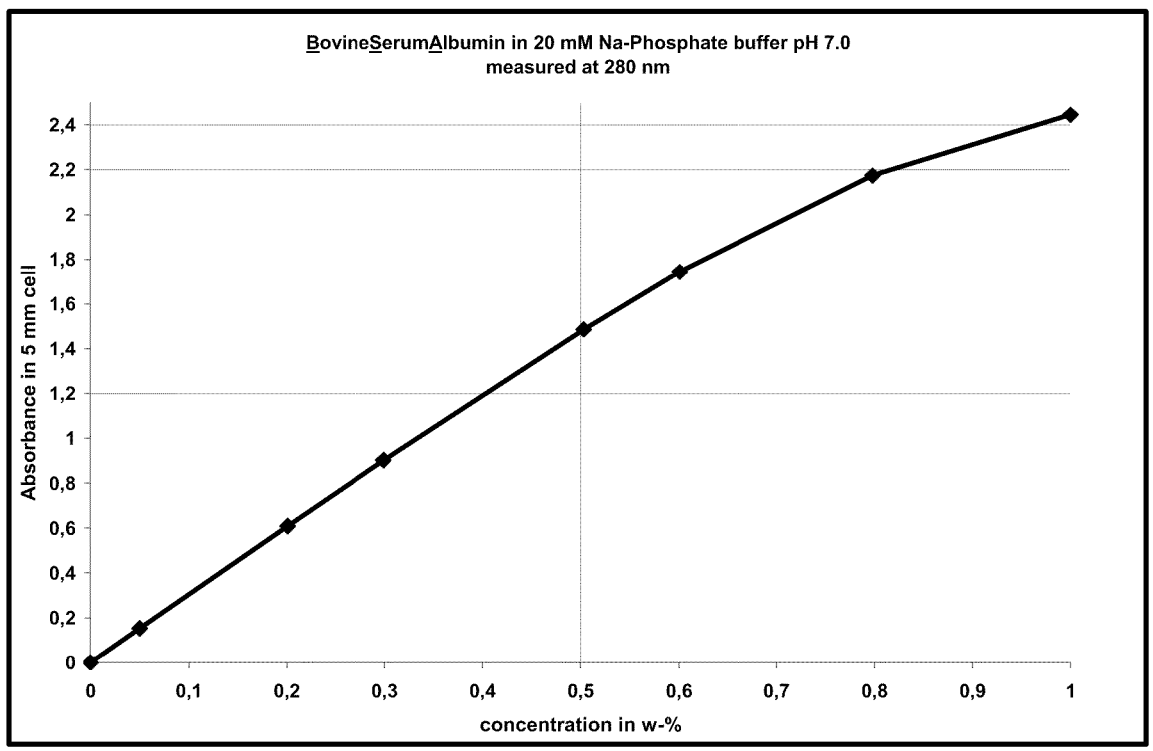
FIG. 5 is a graph showing the linearity of response of a UV-LED detector at 280 nm to a range of concentrations of Bovine Serum Albumin in 20 mM sodium phosphate buffer at pH 7.0.

FIG. 5 shows a dose response curve obtained at 280 nm for a range of concentrations of the protein bovine serum albumin (BSA) using an apparatus according to the invention as described in FIG. 2. BSA was obtained from Sigma (Sigma-Aldrich Inc, MO, USA) and serially diluted in 20 mM sodium phosphate buffer to produce seven solutions ranging in concentration from 0.05 to 1% (by weight). The UV absorbance of each solution was determined in a 5 mm cell path following irradiation at 280 nm using a UVTOP® UV light emitting diode obtained from Sensor Electronic Technology, Inc. and a band pass interference filter with 7 nm bandwidth centered at 280 nm obtained from Omega Optical Inc., USA. As can be seen, a linear response was observed over the range 0.05 to 0.8% (by weight). In stability studies with the 280 nm UV light emitting diode, the LED was found to be stable for at least 12000 hours.

Figure 6:
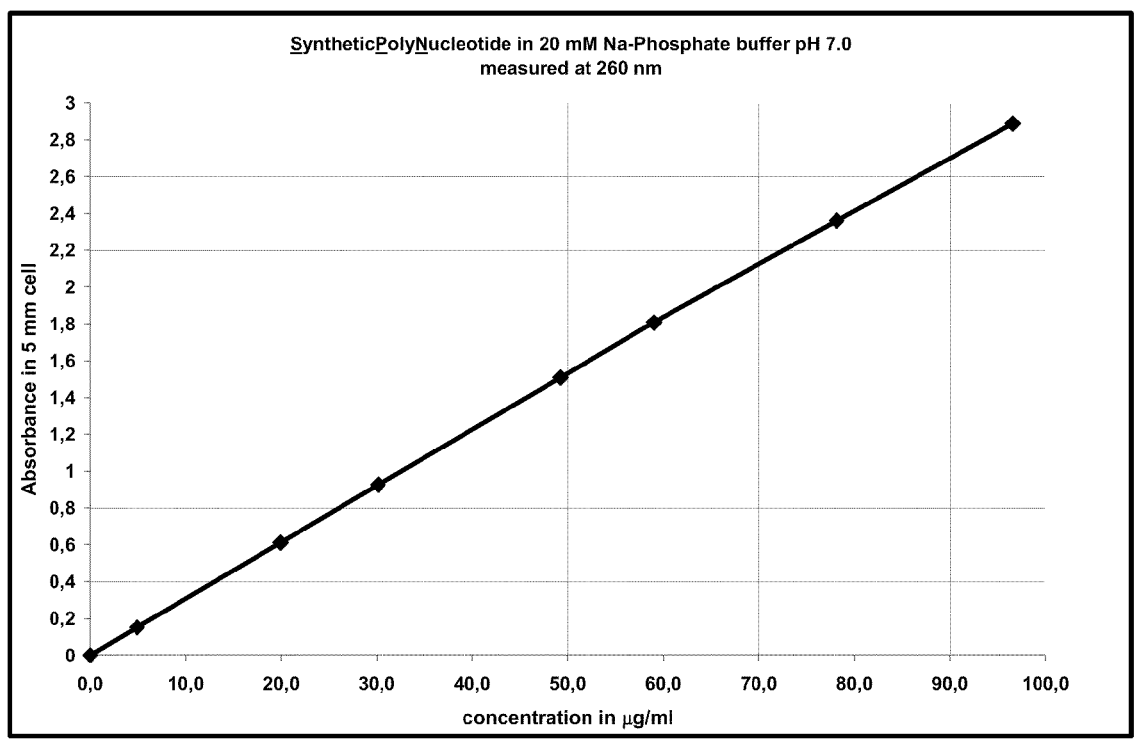
FIG. 6 is a graph demonstrating the linearity of response of a UV-LED detector at 260 nm to a range of concentrations of Synthetic Poly Nucleotide in 20 mM sodium phosphate buffer at pH 7.0.

A dose response curve was obtained for the synthetic polynucleotide (SPN) described above (see FIG. 3) using an apparatus according to the invention (see FIG. 2). The 20 mer SPN was prepared according to the method described by J Shanagar, J. Biochem. Biophys. Methods (2005), 64, 216-225. Seven different concentrations of SPN were prepared ranging from 5 to 97 µg/ml in 20 mM sodium phosphate buffer at pH 7.0. The absorbance of each solution was determined in a 5 mm path length following irradiation at 260 nm using a UVTOP® UV light emitting diode obtained from Sensor Electronic Technology, Inc. and a band pass interference filter with 7 nm bandwidth centered at 260 nm from Omega Optical Inc., USA. The linear response obtained is shown in FIG. 6.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

The invention claimed is:

1. A method for measuring the concentration of a substance in a solution, said substance having an absorption at 300 nm or less, said method comprising:
   i) transmitting ultraviolet light of wavelength 300 nm or less from a light source which light source is a light emitting diode which emits light at a wavelength of 300 nm or less, through a band pass filter;
   ii) passing said ultraviolet light emanating from said band pass filter through a beam-splitter;
   iii) diverting a first portion of the light by the beam-splitter and quantifying the electromagnetic radiation of said first portion with a reference detector to obtain a reference value;
   iv) irradiating a known path length of the solution with a second portion of the light passing through the beam splitter;
   v) quantifying the electromagnetic radiation transmitted through the solution with a sample detector to obtain a sample value; and
   vi) determining the absorbance (A) from said sample value and said reference value and using said absorbance to obtain a measuring value for the concentration by a dose-response curve; wherein said light source is a light emitting diode which emits light of wavelength of 300 nm or less;
   further wherein said substance is separated from one or more compounds present in said solution by chromatography prior to step (i).

2. The method of claim 1, wherein the solution is selected from the group consisting of cell extract, cell lysate and cell culture or mixtures thereof.

3. The method of claim 1, wherein said reference detector and said sample detector is a UV sensitive photomultiplier or a UV sensitive photodiode.

4. The method of claim 1, wherein said substance is a protein or a peptide.

5. The method of claim 1, wherein said substance is a nucleic acid.

6. An apparatus for measuring the concentration of a substance in a solution, said substance having an absorption at 300 nm or less, comprising:
   i) a cell of known path length for containing said solution, said cell being transparent to light of wavelength of 300 nm or less;
   ii) a light source, wherein said light source is a light emitting diode which emits light of wavelength of 300 nm or less;
   iii) a band pass filter;
   iv) a beam splitter for dividing light into a first portion and a second portion;
   v) a reference detector for detecting electromagnetic radiation diverted by said beam splitter;
   vi) a sample detector for detecting the electro magnetic radiation transmitted through said solution; and
   vii) a dose-response curve for determining the absorbance (A) from said sample value and a reference value and using said absorbance to obtain a measuring value for the concentration.

7. The apparatus of claim 6, wherein said reference detector and said sample detector is a UV sensitive photodiode or a UV sensitive photomultiplier.

8. The apparatus of claim 6, further comprising a collimating lens.

9. The apparatus of claim 6, further comprising a focusing lens.

* * * * *